United States Patent [19]

Schwartz et al.

[11] 4,371,619

[45] Feb. 1, 1983

[54] ACETIC ACID BY FERMENTATION

[75] Inventors: Robert D. Schwartz, Concord, Calif.; Frederick A. Keller, Jr., Naperville, Ill.

[73] Assignee: Union Carbide Corporation, Danbury, Conn.

[21] Appl. No.: 162,254

[22] Filed: Jun. 23, 1980

[51] Int. Cl.³ ............................................. C12P 7/54
[52] U.S. Cl. .................................. 435/140; 435/245; 435/842
[58] Field of Search ............... 435/140, 842, 172, 245, 435/253; 426/17

[56] References Cited

U.S. PATENT DOCUMENTS

| | | | |
|---|---|---|---|
| 736,402 | 8/1903 | Jacquemin | 435/245 |
| 1,864,746 | 6/1932 | Legg et al. | 435/140 |
| 1,875,368 | 9/1932 | Christensen et al. | 435/140 |
| 2,386,374 | 10/1975 | Weizmann | 435/842 |

OTHER PUBLICATIONS

J. of Bacteriology, vol. 43, pp. 701–715, 1/42.

Primary Examiner—Hiram Bernstein
Attorney, Agent, or Firm—Bernard Francis Crowe

[57] ABSTRACT

Acetic acid has been prepared by a fermentation process using *Clostridium thermoaceticum* in a varied form obtained by repeated fermentations under anaerobic conditions and low redox potentials at successively more acidic pH's than the original organism.

10 Claims, 1 Drawing Figure

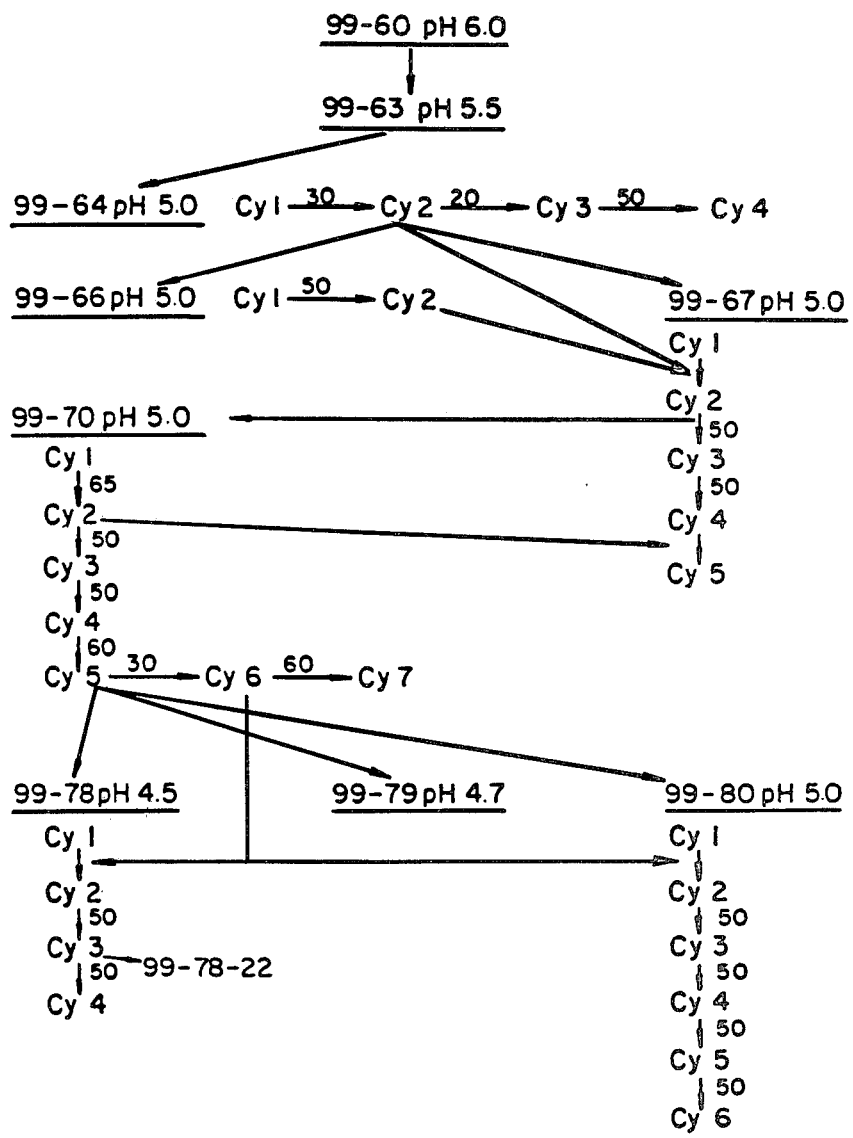

ACETIC ACID BY FERMENTATION

BACKGROUND OF THE INVENTION

This invention pertains to the preparation of acetic acid by the fermentation of an aqueous nutrient medium containing assimilable sources of carbon, nitrogen and inorganic substances and more particularly to the use of a variant of *Clostridium thermoaceticum* at pH's as low as 4.5.

Acetic acid is regularly made by fermentation of sugars. In the course of making wine from grapes, failure to exclude air results in formation of vinegar. The so-called "distilled vinegar" of commerce is made by microbial oxidation of ethanol from either synthetic or fermentation sources.

The vinegar process takes place in two distinct steps. The first is fermentation of the sugar to ethanol with a yeast in yields of about 45%. The second step is a microbial oxidation of the alcohol in the vinegar stock to acetic acid with the organism *Acetobacter aceti* with an efficiency of conversion of about at best 85% of the stoichiometric theoretical. The overall weight yield from sugar to acetic acid with conventional technology is then about 49.5%.

A better process for making acetic acid is suggested by the knowledge of the existence of an organism known as *Clostridium thermoaceticum* which will convert sugars to acetic acid in one step. It is also attractive because it is a thermophile, that is, it grows best at temperatures around 60° C. This reduces competition from contaminating organisms, so that maintaining a pure culture is easier. A large temperature differential from the cooling water is also provided, making heat removal easier. It is a strict anaerobe which is an asset in that the likelihood of contamination is reduced and a liability in that complete elimination of oxygen is necessary if the organism is to grow and function.

Unfortunately this organism only grows well at approximately neutral pH's. Since the product acetic acid reduces the pH, fermentation stops unless the acid is neutralized with a base such as sodium hydroxide. While this will then allow the organism to continue to ferment, it complicates the recovery of the desired product acetic acid because it must be removed as an acetic acid salt and then regenerated to the free acid.

It is therefore an object of this invention to provide a method utilizing *Clostridium thermoaceticum* to produce acetic acid by fermentation of carbohydrate without having to neutralize the acetic acid product.

State another way, it is another object of this invention to provide a form of *Clostridium thermoaceticum* which will grow in an aqueous nutrient at pH's below about 6.

SUMMARY OF THE INVENTION

In the microbiological method of preparing acetic acid by converting carbohydrates to acetic acid by growing *Clostridium thermoaceticum* in an anaerobic fermentor in the presence of an aqueous nutrient, an improvement has been developed which comprises using a variant strain of *Clostridium thermoaceticum*, accession number ATCC 31490, in a batch fermentation at a pH of about 2 to about 5, a temperature of about 45° to 65° C. or preferably 55° to 60° C. and a redox potential E measured with an Ingold Argenthal/Pt electrode of about −50 to about −220 millivolts.

The variant strain of the microrganism *Clostridium thermoaceticum*, accession number ATCC 31490, can be prepared as a biologically pure culture by a method which comprises:

(1) carrying out a series of fermentations at about 58° C. starting with an acetate tolerant strain of *Clostridium thermoaceticum* which grows in an aqueous nutrient medium containing assimilable source of carbon, nitrogen and inorganic substances, at a pH of 6 and allowing batch growth to proceed under anaerobic conditions until about 15.0 grams of acetic acid per liter of nutrient medium are produced;

(2) transferring an aliquot of the growing culture and nutrient medium to a second batch of the same nutrient medium used in step (1) but with a pH of 5.5 and allowing growth to continue until about 16.0 grams of acetic acid per liter of nutrient medium are produced; and (3) continuing successive transfers of aliquots of the growing culture and medium until about 4.5 grams of acetic acid per liter of medium are produced in a culture medium having a pH of about 4.5 and a redox potential E measured with an Ingold Argenthal/Pt electrode of about −220 millivolts.

The variant strain of the microrganism *Clostridium thermoaceticum*, accession number ATCC 31490 as produced hereinabove is a new composition of matter.

Although fermentation temperatures for making acetic acid with this variant strain of *Clostridium thermoaceticum* can range from about 45° to about 65° C., it is preferred to use a temperature of about 55° to 66° C. and most preferred to use a temperature of about 58° to 60° C.

Acetic acid can be produced with this variant strain of microrganism in pH ranges of 2 to about 4.6 and preferably about 4 to 4.5.

It will be understood by those skilled in the art that the redox potential E in fermentations with the variant strain of *Clostridium thermoaceticum* will depend both upon the temperature of the system and the pH as well. Thus for example where the temperature of the system is about 45° C. and the pH about 2, the redox potential can be as low as at least about −27 millivolts. At temperatures of about 45° C. and a pH of about 5 the redox potential can be at least as low as about −216 millivolts. At temperatures of about 65° C. and a pH of about 5, the redox potential can be at least as low as about −236 millivolts. Where the temperature is about 65° C. and a pH of about 2, the redox potential can be at least as low as about −35 millivolts. *Clostridium thermoaceticum* is an obligately anaerobic thermophile that can homoferment one mole of glucose to three moles of acetic acid. Previously available strains of this microorganism preferably carried out this homofermentation at a pH of about 6-8. While this organism provides a potentially attractive alternative to the conventional petrochemical routes to acetic acid, it is not an economically viable one unless several criteria can be met. Among such criteria is the necessity for conducting the fermentation at a pH at least as low as 4.5. This is essential because a strain of *Clostridium thermoaceticum* which is only active at a pH around 7 necessitates controlling the pH of the fermentation system close to neutral. Since acetic acid is the reaction product, the pH of the fermentation medium is progressively lowered as the microorganism grows. This necessitates the addition of a base and isolation of the acetic acid not in a free state but in the form of a salt which must be then regenerated to acetic acid.

DESCRIPTION OF THE INVENTION

The parent microrganism used in preparing the variant strain described in this invention was an acetate tolerant strain, viz., *Clostridium thermoaceticum* 1745 derived from a wild-type of *Clostridium thermoaceticum* obtained from Ljungdahl of the University of Georgia at Athens, Ga. This Ljungdahl culture was subjected to ethylmethane sulfonate mutagenesis and selection on 2% sodium acetate by R. W. Warren of the Union Carbide Technical Center at Tarrytown, N.Y.

Media

For all experiments the medium described in Table I was used supplemented with 20 grams of glucose per liter and $CaCl_2$ (10 ml/l of a 1.6 g/l stock solution) at the time of inoculation, and $CoCl_2 6H_2O$ (10 ml/l of a 4.75 g/l stock solution) and $Fe(NH_4)_2 6H_2O$ (10 ml/l of a 7.84 g/l stock solution) after growth began. 8.5 or 85 ml of medium were introduced into 16×124 mm Hungate tubes (obtained from Bellco Glass, Inc., Vineland, New Jersey) or 124 ml serum bottles, respectively, and fitted with gas impermeable black butyl rubber septa. The Hungate tubes were sealed with screw caps; the serum bottles with an aluminum seal. Next, the tubes and bottles were evacuated until the contents were degassed and boiling sustained for a few minutes, overlayed with anaerobic grade $CO_2$ to a pressure of 10 psig, evacuated again, and sterilized by autoclaving at 15 lbs. for several seconds. Following autoclaving, while the medium was still hot, sterile $CO_2$ was added to 10 psig until the medium reached ambient temperature. This elaborate procedure insured that all measurable traces of oxygen were removed. All stock solutions were treated in the same way. Additions and transfers were made using sterile syringes and needles washed with sterile carbon dioxide. The fermentors (containing 850 ml of medium) were not evacuated and pressurized, but rather sparged with $CO_2$ just prior to and immediately following autoclaving. The supplements, inoculum and sterile water were added to reach a final volume of 10 ml, 100 ml, or 1 liter in the Hungate tubes, serum bottles, or fermentors, respectively.

Storage and Growth Conditions

Hungate tubes containing 3 ml of 6.6% purified agar in water were prepared as above. At the time of use the agar was melted and 7 ml of medium 3098 from Table I containing glucose and calcium chloride and 0.5 ml of the culture to be stored, added. The tubes were stored at ambient temperature or refrigerated. To recover the organism, the agar was macerated with a hypodermic needle, 2 ml of 3098 medium added and the tube incubated at 58°–60° C.

Alternatively, 2 ml of 3098 medium was added to 8 ml of a well grown culture, i.e., $OD_{600}$ 2 or greater, and stored at ambient temperature. To recover the organism a 1:2 to 1:5 dilution into fresh 3098 medium containing glucose and calcium choride was made and the tube incubated at 58°–60° C.

Hungate tubes and serum bottles were incubated in a psycrotherm incubator at 58°–60° C., without agitation (New Brunswick Scientific Co., Edison, N.J.). Fermentors were inoculated with serum bottle grown cultures. The initial pH in the serum bottle was about seven for inocula to be used in pH 7 controlled fermentors, and about 6.5 for inocula to be used in pH 6 controlled fermentors. After growth, the serum bottle culture pH was 6.0–6.5 or 5.5–6.0, respectively.

TABLE 1

| COMPOSITION OF MEDIUM 3098 | |
|---|---|
| Compound | Amount |
| [1]$NaHCO_3$ | 16.8g |
| [1]$K_2HPO_4$ | 7.0g |
| [1]$KH_2PO_4$ | 5.4g |
| Tryptone | 2.5g |
| Yeast extract | 2.5g |
| $(NH_4)_2SO_4$ | 1.0g |
| [1]Sodium thioglycolate | 0.50g |
| $MgSO_4.7H_2O$ | 0.25g |
| p-aminobenzoic acid | 0.20g |
| Sodium Salts Solution | 10.0ml |
| $Na_2WO_4$ | 3.3g |
| $Na_2SeO_3$ | 0.90g |
| $Na_2MoO_4$ | 5.15g |
| Deionized water | 1 liter |
| Vitamin Solution | 10.0ml |
| d-biotin | 0.50g |
| Nicotinic acid | 0.50g |
| Deionized water | 1 liter |
| Trace Salts Solution | 10.0ml |
| EDTA | 500.0mg |
| $MnCl_2.4H_2O$ | 500.0mg |
| $H_3BO_3$ | 10.0mg |
| $ZnSO_4$ | 6.9mg |
| $AlK(SO_4)_2.12H_2O$ | 10.0mg |
| $NiCl_2$ | 2.0mg |
| $CuCl_2.2H_2O$ | 1.0mg |
| Deionized water | 1 liter |
| Deionized water | to yield 850 ml |

[1]For pH controlled fermentors the $NaHCO_3$ was reduced to 6.7g, $KH_2PO_4$ reduced to 0.54g, no $K_2HPO_4$ was added, and thioglycolate added at time of use if needed (10ml/l of a 50g/l stock solution).

Glucose Assay

The glucose concentration was estimated using the hexokinase/glucose-6-phosphate dehydrogenase method. Reagents and procedures were from Calbiochem (La Jolla, Calif.).

Growth

Growth was monitored by measuring the optical density (OD) at 600 nm. A Spectronic 70 was used (Bausch & Lomb, Inc., Rochester, New York). A standard curve relating OD to dry weight was constructed and it was shown that an $OD_{600}$ of 4.0 was equivalent to 1 gram per liter dry weight.

Acetic Acid Assay

Broth samples were clarified by filtration through 0.45 micron filters or by centrifugation at about 30,000 G's for 10 minutes. One ml of clarified broth was added to a 2 ml vial and 70 microliters of a 50% weight/volume solution of orthophosphoric acid added to shift the acetic acid equilibrium to the acid form. Finally, 20 microliters of a 50% weight/volume solution of propanoic acid was added as an internal standard. The vials were then sealed and assayed. Standards containing known amounts of acetic acid were similarly prepared.

Acetic acid was determined gas chromotographically using either a Hewlett-Packard Model 5830-A or a Varian 3700. Both were equipped with a flame ionization detector, automatic sample injector, and integrator. Injection port and detector temperatures were 150° and 300° C., respectively. The column was 10 feet by ⅛ inch 304 stainless-steel passivated with dilute nitric acid and packed with SP-1200 (a low polarity ester type stationary packing containing 1% orthophosphoric acid) plus 1% orthophosphoric acid on acid washed 80/100 mesh Chromasorb W (Supelco, Inc., Bellefont, Pennsylvania). As isothermal temperature of 125° C. was maintained, and the carrier gas flow was 30 ml of helium per minute. A glass insert (washed in 1% phosphoric acid, distilled water rinsed, and air dried) was used as a pre-column by inserting it in the injector body. New columns were conditioned under carrier gas flow and alternate injections of 5 microliters of distilled water and 1% phosphoric acid, spaced 5 to 10 minutes apart, over the course of a day. At the beginning of each day a fresh pre-column and septum were installed and 5 microliters of 1% phosphoric acid injected. At the end of each day, five 10 microliter injections of distilled water were made.

For unknowns and standards 0.4–0.5 microliters were injected. The acetic acid was quantitated by measuring the ratio of the acetic acid peak area to the paek area of the propanoic acid. Each sample was injected 3–5 times and the average concentration of the last 2 or 3 injections recorded. This was required, as a sample with a higher concentration than the previous sample would yield a lower concentration on the first injection or two than actually present, due to unsaturation of the acid sites on the column. This assay is linear to about 2% weight/volume acetic acid with an error of less than 5%. Acetic acid normally elutes in about one minute and propionic acid in 90 seconds. However, the scan was routinely extended to about 4.5 minutes as a partial test of culture integrity.

Carbon Dioxide Purification System

To insure that the carbon dioxide was of the highest purity attainable the following purification and oxygen removal system was used. First, a 600 pound cylinder of instrument grade carbon dioxide (Linde) was "blown down" by opening the cylinder valve completely and venting for 90 seconds, closing the valve, waiting 30 minutes and venting again for 30 seconds. This procedure was recommended by Linde to remove traces of oxygen. Next, a high purity regulator was installed. The gas was then passed through the following system at about 10 psig:

(1) A drying filter (Plexiglass cylinder 12 inches long and 1.25 inches in diameter) where the first 25% of the bed volume was packed with Drierite (W. A. Hammond Drierite Co.), the next 50% with activated carbon, and the last 25% with Drierite. This filter removes moisture and organic impurities.
(2) A glass furnace tube packed with oxidized copper turnings and inserted in a vertical gas purifying furnace operated at about 520° C. This furnace oxidizes reduced compounds in the gas. The copper is regenerated (oxidized) by passing oxygen over the hot copper until it becomes dull black in appearance.
(3) Two glass furnace tubes filled with reduced copper turnings and inserted in gas purifying furnaces heated to about 520° C. These two furnaces adsorb any oxidized compounds in the gas. Eventually, the copper becomes oxidized and is regenerated (reduced) by passing a gas mixture consisting of 97% $CO_2$ and 3% $H_2$ over the hot copper.
(4) A drying filter packed with Drierite, 25%; 4A Linde molecular sieve, 50%; and Drierite, 25%. The above components are connected with 1/8 inch stainless steel tubing that has been washed with methanol to remove grease and oil, and passivated with 10% aqueous nitric acid for 10 minutes to remove other surface impurities and inorganics. The gas thus purified is ready to use for sparging fermentors or overlaying media in Hungate tubes or serum bottles.

For fermentors the gas flow was controlled by calibrated rotometers and the final filter was sterile glass wool. For Hungate tubes and serum bottles a special stainless steel gassing manifold was used so $CO_2$ pressurization and evacuation could be controlled. To enter the tubes or bottles the gas was passed through a Whitey quick opening 1/8 inch tubing valve to which was attached (by tygon tubing) a sterile 0.5 cc glass syringe packed with glass wool and a 1.5 inch sterile needle.

Fermentors

The fermentors were modified jacketed glass spinner flasks with one liter working volumes (Belco Glass Inc. Vineland, N.J.). The modification consisted of:
(1) two additional sidearm ports (four total);
(2) a ground glass condenser attachment port on top;
(3) bolt lock flange and gasket system to seal top and bottom parts.

The pH was controlled with a New Brunswick Scientific Co. Model pH-40 controller plus pump module. Following initial pH adjustment with HCl and/or acetic acid, control was achieved by addition of oxygen free 50% aqueous sodium hydroxide. The redox potential ($E_{measured}$) was monitored with a platinum redox electrode (Ingold) and recorded in millivolts on an Orion Model 701A meter. Carbon dioxide was sparged at the the rate of 0.08 vvm and the fermentors were operated under a positive pressure of 15–25 mm $H_2O$. A temperature of 58° C. was maintained by circulating water from a constant temperature bath through the outer fermentor jacket. Chilled water (10° C.) was circulated through the condenser from a Haake Model KT-33 cooling bath.

It was found desirable on occasion to hold a fermentor in a non-growth, but stable mode. The following procedure was used:

20–30% of the volume in the fermentor was replaced with fresh nutrient medium, the temperature reduced to ambient, the agitator used to keep the fermentor contents homogenous was turned off, the carbon dioxide sparged reduced to a trace of pH control halted. With the addition of fresh media the pH rose about 0.25–0.50 pH units. This procedure was referred to as "banking". Fermentors could be restarted after banking up to as long as 30 days. To re-start, the temperature, pH, pH control, carbon dioxide sparge and agitation were restored to the original conditions. Growth usually resumed within two days. If after two days growth had not resumed, the volume was diluted 30 to 50%. Failure to re-establish growth inevitably coincided with failure to re-establish the required redox potential. Samples were withdrawn using sterling, carbon dioxide washed syringes and the $OD_{600}$, glucose concentration and acetic acid concentration measured.

Preparation of Redox Probes

Redox probes were rountinely cleaned before use in 70 mM sodium hypochlorite solution and checked in a pH 4.0, 0.05 M potassium hydrogen phthalate buffer saturated with quinhydrone (the latter being present in excess). The probes used were stable and had a measurable output ($E_{measured}$) of $+263\pm$a few millivolts at 30° C. in the quinhydrone buffer. This corresponds to an output ($E_h$) of about +460 mV relative to the standard hydrogen electrode. The $E_h$ is obtained by adding 196 mV to the measured output of the Ingold Argenthal/Pt electrode.

The measured output of the Ingold redox probe at a pH and temperature other than 4.0 and 30° C. respectively, may be calculated from the question:

$$E_{measured} = +98.8 - 0.198(T)(pH)$$

where T is the absolute temperature in degrees kelvin.

The invention is further described in the description which follows.

Attempts were made to lower the pH from 6 to 5 using *Clostridium thermoaceticum* 1745. This was the acetate tolerant strain of obligately anaerobic thermophile isolated at Union Carbide Technical Center in Tarrytown, New York at a neutral pH following ethylmethane sulfonate mutagenesis and selection on 2% sodium acetate. This strain can grow at pH 6 and an initial acetic acid concentration greater than 10 grams per liter of nutrient medium. The medium, growth conditions and culture storage conditions have been described above. The estimation of growth, glucose and acetic acid as well as the preparation of anaerobic grade carbon dioxide have also been described above.

The fermentors used were the modified jacketed glass spinner flasks with one liter working volumes described above. The pH was controlled with sodium hydroxide, the redox potential was monitored and the temperature maintained at 58° C. also as described above.

Fed-batch fermentation was used in which the fermentors were cycled by the draw and fill method. Each cycle, usually 50% of the volume was replaced with fresh medium by withdrawing broth with a peristaltic pump and filling, by carbon dioxide washed syringe, with medium from serum bottles. This method was found to present the least risk of introducing oxygen into the fermentor. It should be noted that as the fermentor is cycled, the acetic acid concentration at the beginning of the new cycle is higher than at the beginning of the previous cycle. Four fermentors were operated simultaneously.

Attempts to lower the pH from 6 to 5 at an initial acetic acid concentration of 10 grams per liter of medium failed to result in growth. Lowering the pH from 6 to 4.5 without adding extraneous acetic acid also failed to result in growth. Furthermore, even at a pH of 6, increasing the initial acetic acid concentration above 10-12 grams per liter of medium failed to result in growth.

Success was achieved when, using as an inoculum, cells growing at pH 6 and an initial acetic acid concentration of about 5 grams per liter of medium (Fermentor 99-60), a fermentor was inoculated at pH 5.5 and an initial acetic acid concentration of about 7.5 grams per liter of medium (Fermentor 99-63). The cells grew with a generation time of about 20 hours, and an acetic acid concentration of 16 grams per liter of medium was reached with a conversion efficiency of 77%. This fermentor was not cycled but used to inoculate another fermentor at pH 5 and no added acetic acid (Fermentor 99-64). This fermentor also produced growth. The detailed genealogy, showing how the strain was eventually isolated that could grow and produce acetic acid at pH 4.5 is delineated in the Figure. The acetic acid concentration at the beginning and end of each cycle, the generation time and the efficiency of conversion of glucose to acetic acid for the genealogy shown in the Figure is presented in Table 2. In the geneology for *Clostridium thermoaceticum* 99-78-22(ATCC) 31490), shown in the Figure, the first number 99-x, is the fermentor identification number. The number on the arrow is the percent dilution between cycles (Cy). The culture in 99-60 was *Clostridium thermoaceticum* 1745.

The selective pressures used were pH and acetic acid concentration. For pH pressure, growth was started with cells grown at the lowest pH where growth was previously demonstrated (initially pH 6) and then fermentors were inoculated at an even lower pH (initially pH 5.5 and 5.0). No extraneous acetic acid was added.

For acetic acid pressure fermentation was started with cells grown at an initial acetic acid concentration of 10 grams per liter of medium and gradually increased. The pH was maintained at the lowest pH where growth had been demonstrated (initially pH 6). At least one fermentor was always maintained at the lowest pH where growth would occur and a low acetic acid concentration, i.e., less than 5 grams per liter of medium. This fermentor served as a source of inocula for the other fermentors.

Thus the culture designated as *Clostridium thermoaceticum* 99-22 has been obtained and has been deposited in the American Type Culture Collection in Washington, D.C. The ATCC accession number is 31490.

Although the invention has been described with a certain degree of particularity, it is understood that the present disclosure of the preferred forms has been made only by way of example and that numerous changes can be resorted to without departing from the spirit and the scope of the invention.

TABLE 2

Acetic acid concentration, generation time, and efficiency of conversion of glucose to acetic acid for the pH controlled batch fermentations leading to the isolation of a pH 4.5 tolerant strain.

| Ferm Number | pH | Cycle Number | Acetic Acid, g/l Initial | Acetic Acid, g/l Final | Generation Time, h. | Efficiency to acetic acid, % |
|---|---|---|---|---|---|---|
| 99-60 | 6.0 | 1 | 5.3 | 15.1 | 5 | 76 |
| 99-63 | 5.5 | 1 | 7.4 | 16.0 | 20 | 77 |
| 99-64 | 5.0 | 1 | 0.96 | 4.1 | 12 | 49 |
|  |  | 2 | Too little growth for calculations | | | |
|  |  | 3 | 2.2 | 5.2 | 35 | 55 |
|  |  | 4 | 3.2 | 6.0 | 48 | 80 |
| 99-66 | 5.0 | 1 | 3.7 | 5.4 | 25 | 74 |
|  |  | 2 | 2.6 | 4.8 | 25 | 55 |
| 99-67 | 5.0 | 1 | Redox too high, no growth | | | |
|  |  | 2 | 5.5 | 6.8 | 70 | 87 |
|  |  | 3 | Redox too high, no growth | | | |
|  |  | 4 | Redox too high, no growth | | | |
|  |  | 5 | 1.8 | 5.5 | 30 | 81 |
| 99-70 | 5.0 | 1 | 0.65 | 3.5 | 13 | 71 |
|  |  | 2 | 1.5 | 3.5 | 62 | 67 |
|  |  | 3 | 1.5 | 2.9 | 26 | 78 |
|  |  | 4 | 2.5 | 3.9 | 45 | 93 |
|  |  | 5 | Too little growth for calculations | | | |
|  |  | 6 | 1.7 | 6.4 | 24 | 93 |
|  |  | 7 | 2.5 | 8.0 | 28 | 87 |
| 99-80 | 5.0 | 1 | Redox too high, no growth | | | |
|  |  | 2 | 4.2 | 7.9 | 24 | 67 |
|  |  | 3 | 4.5 | 11.5 | 32 | 84 |
|  |  | 4 | 6.0 | 8.6 | 128 | 87 |
|  |  | 5 | Too little growth for calculations | | | |
|  |  | 6 | 2.5 | 5.0 | 70 | 83 |
| 99-79 | 4.7 | 1 | 0.23 | 6.2 | 17 | 75 |
| 99-78 | 4.5 | 1 | Redox too high, no growth | | | |
|  |  | 2 | 0.50 | 3.4 | 36 | 78 |
|  |  | 3 | 1.7 | 4.5 | 52 | 93 |
|  |  | 4 | 2.2 | 3.9 | 165 | 68 |

What is claimed is:

1. The method of preparing biologically pure culture of a variant strain of the microorganism *Clostridium thermoaceticum* 99-78-22, accession number ATC 31490, which comprises the steps of:
   (1) carrying out a series of fermentations at about 58° C. starting with an acetate tolerant strain of *Clostridium thermoaceticum* which grows in an aqueous nutrient medium containing assimilable sources of carbon, nitrogen and inorganic substances, at a pH of 6 and allowing batch growth to proceed under anaerobic conditions until about 15.0 grams of acetic acid per liter of nutrient medium is produced;
   (2) transferring an aliquot of the growing culture to a second batch of the same nutrient as in step (1) but with a pH of 5.5 and allowing growth to continue until 16.0 grams of acetic acid per liter of nutrient is produced; and
   (3) continuing successive transfers of aliquots of the growing culture medium until about 4.5 grams of acetic acid per liter of nutrient are produced having a pH of 4.5 and a redox potential E, measured with an Ingold Argenthal/Pt electrode of about −220 millivolts.

2. Method claimed in claim 1 wherein the culture having a pH of 4.5 was cycled twice with two 50% volume dilutions and the active culture of *Clostridium thermoaceticum* isolated after a 52 hour generation time in a medium containing 4.5 grams of acetic acid per liter of medium.

3. A biologically pure culture of a variant strain of the microorganism *Clostridium thermoaceticum* identified as 99-78-22, accession number ATCC 31490, said culture being capable of producing acetic acid at a pH of about 4.5, a temperature of about 58° C. and a redox potential E measured with an Ingold Argenthal/Pt electrode at least as low as −220 millivolts in an aqueous nutrient medium containing assimilable sources of carbon, nitrogen and inorganic substances.

4. In a method for converting carbohydrates to acetic acid by growing *Clostridium thermoaceticum* in an anaerobic fermentor in the presence of an aqueous nutrient medium containing assimilable sources of carbon, nitrogen and inorganic substances, the improvement which comprises using a biologically pure culture of a variant strain of *Clostridium thermoaceticum* number 99-78-22, accession number ATCC 31490 in a pH controlled fed-batch fermentation at pH 4.5 at a temperature of about 58° C. and initial acetic acid content of about 1.7 grams per liter of nutrient for a time sufficient to produce at least 4.5 grams of acetic acid per liter at a redox potential measured with an Ingold Argenthal/Pt electrode of about −220 millivolts.

5. Method claimed in claim 4 wherein the temperature is about 45° to 65° C.

6. Method claimed in claim 4 wherein the temperature is about 55° to 60° C.

7. Method claimed in claim 4 wherein the temperature is about 45° C. and the redox potential at pH 2 measured with an Ingold Argenthal/Pt electrode of at least −27 millivolts.

8. Method claimed in claim 4 wherein the temperature is about 65° C., the pH about 2 and the redox potential measured with an Ingold Argenthal/Pt electrode of about −35 millivolts.

9. Method claimed in claim 4 wherein the temperature is about 45° C., the pH about 5 and the redox potential E measured with an Ingold Argenthal/Pt electrode is about −216 millivolts.

10. Method claimed in claim 4 wherein the temperature is about 65° C., the pH about 5 and the redox potential E measured with an Ingold Argenthal/Pt electrode is about −236 millivolts.

* * * * *